(12) United States Patent
He et al.

(10) Patent No.: US 11,555,808 B2
(45) Date of Patent: Jan. 17, 2023

(54) WIDE-CONCENTRATION MULTI-COMPONENT HAZARDOUS GAS DETECTOR AND IMPLEMENTATION METHOD THEREOF

(71) Applicant: SICHUAN FIRE RESEARCH INSTITUTE OF MEM, Chengdu (CN)

(72) Inventors: Jin He, Chengdu (CN); Haidong Guo, Chengdu (CN); Han Zhang, Chengdu (CN); Junjun Liu, Chengdu (CN); Lun Zhou, Chengdu (CN); Zejiang Zhang, Chengdu (CN)

(73) Assignee: SICHUAN FIRE RESEARCH INSTITUTE OF MEM, Chengdu (CN)

( * ) Notice: Subject to any disclaimer, the term of this patent is extended or adjusted under 35 U.S.C. 154(b) by 451 days.

(21) Appl. No.: 16/689,085

(22) Filed: Nov. 20, 2019

(65) Prior Publication Data

US 2020/0400632 A1 Dec. 24, 2020

(30) Foreign Application Priority Data

Jun. 20, 2019 (CN) .......................... 201910539143.2

(51) Int. Cl.
*G01N 33/00* (2006.01)

(52) U.S. Cl.
CPC ....... *G01N 33/0031* (2013.01); *G01N 33/007* (2013.01); *G01N 33/0018* (2013.01); *G01N 33/0063* (2013.01); *G01N 33/0073* (2013.01)

(58) Field of Classification Search
CPC ............ G01N 33/0031; G01N 33/006; G01N 27/4077; G01N 27/12; G01N 27/407;
(Continued)

(56) References Cited

U.S. PATENT DOCUMENTS

| 4,606,219 A | 8/1986 | Bout et al. |
|---|---|---|
| 7,504,958 B1 | 3/2009 | Genovese et al. |
| 2007/0269346 A1* | 11/2007 | Wohltjen ........... G01N 33/0014 422/83 |
| 2010/0195669 A1* | 8/2010 | Tzeng ..................... H04J 13/10 370/479 |

(Continued)

FOREIGN PATENT DOCUMENTS

| CN | 201382920 Y | * | 1/2010 |
|---|---|---|---|
| CN | 103914023 A | * | 7/2014 |

(Continued)

*Primary Examiner* — John Fitzgerald
*Assistant Examiner* — Truong D Phan

(57) ABSTRACT

The disclosure discloses a wide-concentration multi-component hazardous gas detector and an implementation method thereof, solving the problems of the existing technology that false negative results, ultra-limit concentration and sensor poisoning often occur in a gas detector used in fire fighting forces. The wide-concentration multi-component hazardous gas detector includes a gas diluting and sampling connector, a sensor integrated module, electrochemical sensors, ADC (analog to digital converter) circuits, MCU (microprogrammed control unit) single chip microcomputers, acousto-optic alarms, a 4-button keyboard module, an LED (light-emitting diode) display module, an SD card data memory module, a power supply control and electric quantity display module, a high-performance lithium battery pack, a small evacuation pump, 433M signal transmission modules and a remote command platform signal collection terminal.

8 Claims, 8 Drawing Sheets

(58) Field of Classification Search
CPC .... G01N 27/414; G01N 33/005; G01N 27/16; G01N 7/06; G01N 1/24; G01N 33/0009; G01N 33/0011; G01N 33/0018; G01N 27/20; G01N 27/24; G01N 27/3274; G01N 33/0006; G01N 33/007; G01N 24/084; G01N 33/0057; G01N 33/22; G01N 33/227; G01N 25/72; G01N 27/61; H01L 2224/48229; H01L 2924/01079; H01L 23/293; H01L 2924/01078; H05K 7/142; H05K 3/301; G06F 1/184; G01M 15/102; G01F 15/0755; G01F 1/34; G08B 21/18; G08B 21/182; H01M 2250/10; H01M 8/04201; H01M 8/04388; H01M 8/04753; G01D 11/24; G01D 11/245; G01L 19/14

See application file for complete search history.

(56) References Cited

U.S. PATENT DOCUMENTS

| | | | | |
|---|---|---|---|---|
| 2011/0172504 | A1* | 7/2011 | Wegerich | A61B 5/7264 600/301 |
| 2015/0295705 | A1* | 10/2015 | Khoshnood | H02J 13/00017 375/257 |
| 2015/0323510 | A1* | 11/2015 | Huynh | G01N 33/0031 73/23.34 |
| 2019/0086378 | A1* | 3/2019 | Holdcroft | G01N 33/0009 |

FOREIGN PATENT DOCUMENTS

| | | | |
|---|---|---|---|
| CN | 105716932 A | * | 6/2016 |
| CN | 206311540 U | * | 7/2017 |
| CN | 208902681 A | | 5/2019 |
| CN | 110186984 A | | 8/2019 |

* cited by examiner

WIDE-CONCENTRATION MULTI-COMPONENT HAZARDOUS GAS DETECTOR AND IMPLEMENTATION METHOD THEREOF

CROSS-REFERENCE TO RELATED APPLICATIONS

This application claims priority to Chinese Patent Application No. 201910539143.2 with a filing date of Jun. 20, 2019. The content of the aforementioned applications, including any intervening amendments thereto, are incorporated herein by reference.

TECHNICAL FIELD

The disclosure relates to a wide-concentration multi-component hazardous gas detector and an implementation method thereof.

BACKGROUND OF THE PRESENT INVENTION

At present, the most commonly used hazardous gas detection equipment in fire fighting forces mainly includes a four-in-one gas detector and a combustible gas detector. The four-in-one gas detector is applicable to on-site detection in multiple sites such as chemical industry, petrochemical industry, coal and municipal gas, can achieve measurement needs of special occasions to perform gas concentration detection or leakage detection on tunnels, pipelines, tanks, sealed windows and the like. The combustible gas detector is a general detector for detecting and measuring multiple hazardous gases, is applicable to detection of toxic gases and corrosive gases in temporary occasions and has the characteristic of simple operation.

However, a portable gas instrument that is commercially available and is equipped in fire fighting forces can detect a small number of gases, and generally only can detect oxygen, carbon monoxide, carbon dioxide and methane. But, there are many kinds of hazardous gases in a fire scene, high-toxic lethal gases mainly include hydrogen cyanide, hydrogen chloride, chlorine and phosgene, and flammable and explosive gases include propane and benzene. A portable gas analyzer equipped in fire fighting forces cannot meet detection needs of hazardous chemicals accident sites, and at the same time various gas detectors have their fixed detection ranges. The instruments can be ensured to be correctly determined only when it completes measurement within its determination range. The gas detection equipment existing in the market and equipped in fire fighting forces are all designed for daily gas micro-leakage monitoring alarm and environmental pollution monitoring with a narrow detectable gas concentration range. When hazardous chemicals are leaked in large quantities and tire accidents occur, the concentration of hazardous gases is often hundreds or thousands times that of daily micro-leakage. The gas detector equipped in fire fighting forces often generates concentration false alarm, sensor poisoning and the like often occur in the gas detector equipped in fire fighting forces, and therefore is not applicable to use during emergency rescue. At the same time, the instrument mainly depends on imports, and therefore is expensive in price and difficult in later maintenance, and has no detailed Chinese information and professional training. False positive test results, false negative test results and concentration misjudgment often occur due to non-standard instrument operation of fire fighters. Such errors are fatal to rescue workers on the spot.

Therefore, it is urgent for those skilled in the art to design a wide-concentration multi-component hazardous gas detector and an implementation method thereof to solve the above-mentioned technical problems.

SUMMARY OF PRESENT INVENTION

The technical problem to be solved by the disclosure is to provide a wide-concentration multi-component hazardous gas detector and an implementation method thereof so as to solve the problems of the existing technology that false negative results, ultra-limit concentration and sensor poisoning often occur in a gas detector equipped in fire fighting forces.

In order to realize the above objective, the disclosure adopts the following technical solution:

A wide-concentration multi-component hazardous gas detector, including a gas detector body, a gas diluting and sampling connector disposed in the gas detector body for diluting the concentration of a to-be-detected gas to enlarge the gas concentration detection range to avoid the poisoning and failure of a sensor, a sensor integrated module plugged-in on the gas detector body and in pipeline connection with the gas diluting and sampling connector and used for integrating a multiple electrochemical sensor without mutual inter-crosstalk so as to detect gases, a ADC circuit disposed within the gas detector body in the same amount with the electrochemical sensors and respectively connected with the sensor integrated module, MCU singlechip disposed within the gas detector body and respectively connected with the ADC circuit through a SPI (serial peripheral interface) bus, a acousto-optic alarm, a 4-button keyboard module and an LED display module disposed on the gas detector body and respectively connected with the MCU singlechip, an SD card data storage module disposed within the gas detector body and exchanging data with the MCU singlechip, a high-performance lithium battery pack disposed within the gas detector body and connected with the MCU singlechip through power supply control and an electric quantity display module, and a remote command platform signal collection terminal;

a small evacuation pump connected with the MCU singlechip is disposed on a pipeline where the gas diluting and sampling connector is connected with the sensor integrated module, the MCU singlechip is in wireless connection with the remote command platform signal collection terminal through a 433 Mhz signal transmission module, and the MCU singlechip is connected with the sensor integrated module.

Further, the gas diluting and sampling connector includes a shell present as a tubular structure, a front cover and a rear cover connected with the top and the bottom of the shell through screw threads, a gas inlet formed on the front cover, a gas outlet formed on the rear cover, a sampling column disposed in the inside of the shell and coaxial to the shell, a filtration module disposed around the outside of the sampling column and used for forming clean air, a first porous barrier detachably disposed at the upper inside of the shell and used for shunting a sampling gas to the sampling column and the filtration module, a porous fiber column disposed on the upper part of the sampling column and used for filtering fine particles in the sampling gas, a sample gas sampling hole formed on the lower part of the sampling column and connected with the porous fiber column, a second porous barrier disposed at the lower inside of the shell and used for conducting the sampling gas and the clean air, and the gas outlet is connected with the sensor integrated module through the pipeline;

a cavity formed by the front cover and the first porous barrier is provided with a pre-filtration module, the pre-filtration module is a sintered Polypropylene fiber filtration core and used for filtering dust and oil particles in a sampling gas, a pressure spring is disposed between the front cover and the first porous barrier, and the pressure spring is located in an interspace formed between the pressure module and the inner side wall of the shell.

Further, a cavity formed by the second porous barrier and the rear cover is provided with a pressure sensor for detecting the operation condition of the gas diluting and sampling connector, the filtration module includes a first filtration module, a second filtration module, a third filtration module and a fourth filtration module which are disposed in sequence from top to bottom and in seal connection through an O-shaped rings (38), the first filtration module is filled with a mixture of a potassium permanganate active alumina column and basic coaly activated carbon, the second filtration module is filled with a refined filtration core made of non-woven paper, the third filtration module is filled with palladium catalyzed aluminum oxide particles and the fourth filtration module is filled with cocoanut active charcoal particles having a high iodine value.

the first filtration module is a ring-shaped box body, and the upper end surface and the lower end surface of the box body are of a porous structure, structures of the second filtration module, the third filtration module and the fourth filtration module are the same with that of the first filtration module; the shell is made of a transparent material, or is provided with a transparent observation zone.

Further, a method for using the gas diluting and sampling connector includes the following steps:

Step A: allowing a sample gas to enter into the inside of the shell via a gas inlet, where the sample gas is filtered with dust and oil particles in the sample gas through the pre-filtration module, and the sample gas is divided into two parts after passing through the first porous barrier, wherein one part of which flows into the filtration modules, and the other part of which flows into a sampling column;

Step B: the sample gas forms the clean air after multistage filtration in the filtration modules and the formed clean air enters the cavity formed by the second porous barrier and the rear cover;

Step C: the sample gas entering into the sampling column is filled with fine particles in the porous fiber column, and finally enters into the cavity formed by the second porous barrier and the rear cover via the sample gas sampling hole; and Step D: in this cavity, the clean air is mixed air with the sample gas in a certain dilution proportion and finally the diluted sample gas are discharged through the gas outlet, wherein the dilution proportion is determined based on the size of the sample gas sampling hole to achieve the purpose of diluting the sample gas.

Further, the sensor integration module includes a circuit board integrated with eight electrochemical sensors, a gas circuit communication mechanism and a sealing gas measurement box, wherein the circuit board is integrated with eight automatic identification and failure detection circuits of the electrochemical sensors in one-to-one correspondence to the eight electrochemical sensors, each of the electrochemical sensors is respectively accessed into the corresponding automatic identification and failure detection circuit of the electrochemical sensors;

the gas circuit communication mechanism is provided with a gas inlet pipe, two gas outlet pipes and eight unitary gas chambers, wherein the gas inlet pipe is respectively communicated with eight unitary gas chambers through the pipeline, each of the gas outlet pipes is respectively communicated with four unitary gas chambers through the pipeline, the eight gas unitary gas chambers respectively correspond to the eight electrochemical sensors, the circuit board is sealed and covered on the gas circuit communication mechanism, and each of the electrochemical sensors is respectively located inside the corresponding the unitary gas chamber;

the sealing gas measurement box includes a box body and a cover body covering the box body, the gas circuit communication mechanism sealed and covered by the circuit board is disposed within the box body, the box body is provided with a gas inlet pipe hole corresponding to the gas inlet pipe and a gas outlet pipe hole corresponding to the gas outlet pipe, the box body is provided with a plug wire hole, the circuit board is provided with an plug wire end respectively connected with the automatic identification and failure detection circuits of the eight electrochemical sensors, the plug wire end penetrates through the plug wire hole to be connected with the ADC circuit; the ADC circuit is provided with eight, each of the ADC circuits is respectively connected with one of the automatic identification and failure detection circuits of the eight electrochemical sensors through the plug wire end, and the gas inlet pipe penetrates through the gas outlet hole to be communicated with the gas outlet hole.

Further, the circuit board is fixedly connected with the gas circuit communication mechanism through a bolt, a silica gel seal ring is disposed between the gas circuit communication mechanism and the circuit board, and the circuit board and the gas circuit communication mechanism are sealed through the silica gel seal ring, and the gas circuit communication mechanism, the box body and the cover body are all made of resin;

one side of the box body is provided with a plug-in protrusion, and the gas inlet pipe hole and the plug wire hole are both provided with the plug-in protrusions, the plug wire end is located at the plug-in protrusion, the bottom surface of the box body is provided with a plug-in dovetail groove, the gas detector body is provided with a socket dovetail groove matched with the plug-in dovetail groove, the sealing gas measurement box is plugged in with the gas detector body through the plug-in dovetail groove, the gas detector body is provided with a plug-in port, and the gas outlet and all the ADC circuits are located within the plug-in port; when the sealing gas measurement box is plugged onto the gas detector body, the plug-in protrusion is plugged into the plug-in port, and the eight automatic identification and failure detection circuits of the electrochemical sensors are respectively connected with eight ADC circuit through the plug wire end, the automatic identification and failure detection circuits of the eight electrochemical sensors are also respectively connected with the MCU singlechip through the plug wire end, and the gas inlet pipe is communicated with the gas outlet.

Further, the automatic identification and failure detection circuits of the electrochemical sensors are used to automatically identify the electrochemical sensors and perform failure detection on the identified electrochemical sensors;

the automatic identification and failure detection circuits of the electrochemical sensors includes an electrochemical sensor access end provided with a CE pin access end, a RE pin access end and a WE pin access end, a programmable and adjustable resistor U1, an MOS transistor Q1, a resistor R1, a resistor R2, a resistor R3, a resistor R4, a resistor R5, a capacitor C1, a capacitor C2, a capacitor C3, a capacitor C5, an amplifier OP1, an automatic gain adjustment circuit and an automatic bias generating circuit, wherein the CE access end, the RE access end and the WE access end are respectively used to couple a CE pin, a RE pin and a WE pin of the electrochemical sensor;

three pins of the electrochemical sensor are respectively connected with the CE pin access the RE pin access end and the WE pin access end;

the CE pin access end, the resistor R1 and an output terminal of the amplifier OP1 are successively connected in series, the RE pin access end, the resistor R2, the resistor R3 and the noninventing input terminal of the amplifier OP1 are successively connected in series, the WE pin access end, the programmable and adjustable resistor U1, the automatic gain adjustment circuit, the resistor R4, the resistor R5 and the inverting input terminal of the amplifier OP1 are successively connected in series;

both ends of the capacitor C1 are respectively connected with the CE pin access end and the RE pin access end, and both ends of the capacitor C3 are respectively connected with the noninventing input terminal of the amplifier OP1 and the output terminal of the amplifier OP1; one end of the capacitor C5 is connected with the programmable and adjustable U1, and the other end of the capacitor C5 is in ground connection; one end of the capacitor C2 is connected between the resistor R2 and the resistor R3, and the other end of the capacitor C2 is connected between the resistor R1 and the output terminal of the amplifier OP1;

the automatic bias generating circuit is connected with the inverting input terminal of the amplifier OP1 and is also in ground connection, a drain electrode D of the MOS transistor Q1 is connected with the WE pin access end, a source electrode S of the MOS transistor Q1 is connected with the RE pin access end, a gate electrode G of the MOS transistor Q1 and the automatic bias generating circuit are respectively connected with one pin of the MCU singlechip, one pin of the MCU singlechip is connected between the resistor R4 and the resistor R5, and the automatic gain adjustment circuit is connected with the MCU singlechip through the ADC circuit;

the automatic gain adjustment circuit includes an amplifier OP2, a programmable and adjustable resistor U3, a programmable and adjustable resistor U4, a programmable and adjustable resistor U5 and a capacitor C6, wherein the inverting input terminal of the amplifier OP2, the programmable and adjustable resistor U3, the programmable and adjustable resistor U4, the programmable and adjustable resistor OP5 and the output terminal of the amplifier OP2 are successively connected in series, both ends of the capacitor C6 are respectively connected with the inverting input terminal of the amplifier OP2 and the output terminal of the amplifier OP2, the inverting input terminal of the amplifier OP2 is connected with the programmable and adjustable resistor U1, the noninventing input terminal of the amplifier OP2 is connected with the resistor R4, and the output terminal of the amplifier OP2 is connected with the MCU singlechip through the ADC circuit;

the automatic bias generating circuit includes an MOS transistor Q2, programmable and adjustable resistor U2, a programmable and adjustable resistor U6 and a capacitor C4, wherein the drain electrode D of the MOS transistor Q2, the capacitor C4, the programmable and adjustable resistor U6, the programmable and adjustable resistor U2 and the source electrode S of the MOS transistor Q2 are successively connected in series, the drain electrode D of the MOS transistor Q2 is connected with the inverting input terminal of the amplifier OP1, the gate electrode G of the MOS transistor Q2 is connected with one pin of the MCU singlechip, and there is a ground connection between the capacitor C4 and the programmable and adjustable resistor U6;

the programmable and adjustable resistor U1 is an X9C102 programmable resistor with a resistance value adjustable range of 0-1 KΩ, the programmable and adjustable resistor U2, the programmable and adjustable resistor U3, the programmable and adjustable resistor U4, the programmable and adjustable resistor U5 and the programmable and adjustable resistor U6 are all X9C104 programmable resistors with a resistance value adjustable range of 0-100 KΩ;

the resistance value of the resistor R1 is 1 KΩ the resistance value of the resistor R2 is 10 KΩ the resistance value of the resistor R3 is 10 KΩ the resistance value of the resistor R4 is 47.5 KΩ and the resistance value of the resistor R5 is 27.4 KΩ; the capacitor C1 is a 10 nf capacitor, the capacitor C2 is a 10 nf capacitor, the capacitor C3 is a 10 nf capacitor, the capacitor. C4 is a 10 nf capacitor, and the capacitor C5 is a 100 nf capacitor.

Further, a method for automatically identifying an electrochemical sensor using the automatic identification and failure detection circuits of the electrochemical sensors comprises the following steps:

Step ①: storing official information of the electrochemical sensor for fire protection in a storage, and establishing an electrochemical sensor database;

Step ②: detecting a no-load output value of a to-be-identified electrochemical sensor in an actual system and a characteristic value of an output curve during power-on process through manual testing on the to-be-identified electrochemical sensor, and recording the tested no-load output value and the characteristic value into the storage;

Step ③: accessing the to-be-identified electrochemical sensor into the automatic identification and failure detection circuits of the electrochemical sensors, powering on the MCU singlechip, and the MCU singlechip reads the no-load output value and the characteristic value of the to-be-identified electrochemical sensor from the storage;

Step ④: the MCU singlechip respectively performs correct configuration on the automatic identification and failure detection circuits of the electrochemical sensors according to the no-load output value and the characteristic value of the to-be-identified electrochemical sensor; and Step ⑤: the MCU singlechip identifies the power-on of the to-be-identified electrochemical sensor through the automatic identification and failure detection circuits of the electrochemical sensors, and monitors the voltage values of the to-be-identified electrochemical sensor at each period of time during the power-on process through the ADC circuit meanwhile matching the monitored voltage values with the electrochemical sensors in the electrochemical sensor database in the storage, thereby automatically identifying the to-be-identified electrochemical sensor.

Further, a method for performing failure detection on an electrochemical sensor using the automatic identification and failure detection circuits of the electrochemical sensors comprises the following steps:

Step I: accessing the to-be-identified electrochemical sensor into an automatic identification and failure detection system of the electrochemical sensor, and starting the automatic identification and failure detection system of the electrochemical sensor;

Step II: initializing the automatic identification and failure detection system of the electrochemical sensor;

Step III: changing the parameters of the automatic identification and failure detection system of the electrochemical sensor to allow a generation of ±1 mv perturbance in a bias of the to-be-detected electrochemical sensor;

Step IV: detecting whether the output voltage of the automatic identification and failure detection system of the electrochemical sensor changes with the perturbance in the bias of the to-be-detected electrochemical sensor, wherein if the output voltage has a large perturbance amplitude, the to-be-detected electrochemical sensor is detected as normal; if the output voltage has a small perturbance amplitude, the to-be-detected electrochemical sensor is detected as failure.

An implementation method of a wide-concentration multi-component hazardous gas detector includes the following steps:

Step 1: selecting an appropriate sensor module according to situations of an accident site, and starting a host;

Step 2: starting an automatic identification and failure detection circuit of an electrochemical sensor to automatically identify the electrochemical sensor, whereby a automatic identification and failure detection system automatically determines the sensor module in use and a operation state of the sensor module in use;

Step 3: performing time-validity detection on the electrochemical sensor using the automatic identification and failure detection circuit of the electrochemical sensor, thereby selecting an electrochemical sensor capable of normal operation, and connecting an unitary gas chambers equipped with the electrochemical sensor to form a passage;

Step 4: placing a gas diluting and sampling connector in a to-be-detected hazardous gas meanwhile starting a small evacuation pump into pump the diluted hazardous gas to the passage of the sensor integrated module;

Step 5: an MCU singlechip respectively performs by starting the electrochemical sensor in the passage every 1 second, performs cross sensitivity calculating and processing on the electrochemical sensor on data obtained by the sampling, wherein the calculated results are displayed in real time through an LED display module and meanwhile the calculated and processed date is stored through an SD card data storage module.

Compared with the prior art, the disclosure has the following beneficial effects:

The wide-concentration multi-component hazardous gas detector of the disclosure is simple in structure, scientific and reasonable in design and convenient to use, can automatically identify electrochemical sensors before gas detection, and performs effectiveness detection, and can effectively eradicate concentration false alarm of sensors; at the same time, the gas diluting and sampling connector can dilute the high-concentration hazardous gas to prevent the poisoning of the electrochemical sensor, thereby effectively widening the concentration range of gas detection; multiple unitary gas chambers are disposed in the sensor integrated module, and one electrochemical sensor is distributed in each unitary gas chamber to detect a hazardous gas; the sensor module of the electrochemical sensor can be replaced according to gas components required to be measured in a disaster site, so as to realize a function of instantly expanding the varieties of the detectable gas; the wide-concentration multi-component hazardous gas detector is applicable to emergency monitoring of hazardous gases in unknown disasters; sampling results can be processed by cross-sensitivity operation of electrochemical gas sensors, so that the detection results are more precise.

Figure 1:
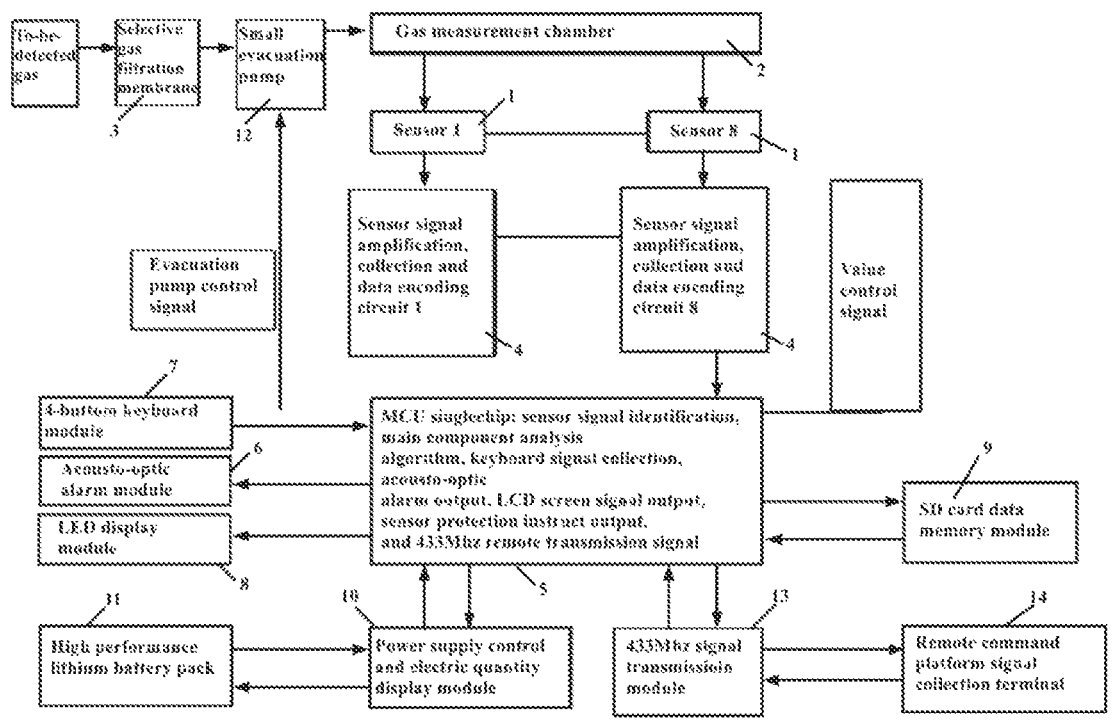
FIG. 1 is a diagram of a structure of a wide-concentration multi-component hazardous gas detector according to the disclosure.

Where, names corresponding to reference numerals are as follows:

1—electrochemical sensor, 2—sensor integrated module, 3—gas diluting and sampling connector, 4—ADC circuit, 5—MCU singlechip, 6—acousto-optic alarm, 7—4-button keyboard modules, 8—LED display module, 9—SD card data storage module, 10—power supply control and electric quantity display module, 11—high performance lithium battery pack, 12—small evacuation pump, 13—433 Mhz signal transmission module, 14—remote command platform signal acquisition terminal, 22—circuit board, 23—gas circuit communication mechanism, 24—sealing gas measurement box, 25—gas inlet pipe, 26—gas outlet pipe, 27—unitary gas chamber, 28—box body, 29—cover body, 210—gas outlet hole, 211—insertion hole, 212—gas inlet pipe hole, 213—plug-in protrusion, 214—plug-in dovetail groove, 215—plug wire end, 31—front cover, 32—shell, 33—rear cover, 34—pressure sensor, 35—pressure spring, 36—first porous barrier, 37—filtration module, 38—O-shaped ring, 39—gas inlet, 310—second porous barrier, 311—sampling column, 312—sample gas sampling hole, 313—porous fiber column, 314—gas outlet, 315—pre-filtration module, 316—observation zone, 371—first filtration module, 372—second filtration module, 373—third filtration module, and 374—fourth filtration module.

DETAILED DESCRIPTION OF PREFERRED EMBODIMENTS

The disclosure will be further described in combination with accompanying drawings and examples. Embodiments of the disclosure include but are not limited to the following examples.

As shown, in FIG. 1, a wide-concentration multi-component hazardous gas detector provided by the disclosure is simple in structure, scientific and reasonable in design and convenient to use. The wide-concentration multi-component hazardous gas detector can automatically identify an electrochemical sensor before gas detection and performs effectiveness detection, and can effectively eradicate the concentration false alarm of the sensor. At the same time, a gas diluting and sampling connector can dilute a high-concentration hazardous gas to prevent the poisoning of the electrochemical sensor, and can effectively widen the detection range of gas concentration. Multiple unitary gas chambers are disposed in the sensor integrated module, and one electrochemical sensor is distributed in each unitary gas chamber to detect a hazardous gas: the electrochemical sensor can detect 8 kinds of hazardous gasses at most, including HCN, HCl, $SO_2$, $NO_2$, CO, NO and $H_2S$ with a wide gas detection range. Sampling results can be processed by cross-sensitivity operation of electrochemical gas sensors, so that the detection results are more precise.

A wide-concentration multi-component hazardous gas detector includes a gas detector body, a gas diluting and sampling connector 3 disposed in, the gas detector body for diluting the concentration of a to-be-detected gas to enlarge the gas concentration detection range to avoid the poisoning and failure of a sensor, a sensor integrated module 2 inserted on the gas detector body and in pipeline connection with the gas diluting and sampling connector for integrating multiple electrochemical sensors 1 that do not generate inter-crosstalk to detect gases, the ADC circuit 4 disposed in the gas detector body, having the same amount with the electrochemical sensors and respectively connected with the sensor integrated module 2, the MCU singlechip 5 disposed in the gas detector body and respectively connected with the ADC circuit 4 through SPI buses, a acousto-optic alarms 6 disposed on the gas detector body and respectively connected with the MCU singlechip 5, a 4-button keyboard module 7, an LED display module 8, an SD card data storage module 9 disposed in the gas detector body and exchanging data with the MCU singlechip 5, a high-performance lithium battery pack 11 disposed in the gas detector body and connected with the MCU singlechip 5 through the power supply control and electric quantity display module 10, and a remote command platform signal collection terminal 14; a small evacuation pump 12 is disposed on a pipeline where the gas diluting and sampling connector 3 is connected with the sensor integrated module 2, the MCU singlechip 5 is in wireless connection with the remote command platform signal collection terminal 14 through a 433 Mhz signal transmission module 13, and the MCU singlechip 5 are connected with the sensor integrated module 2.

Figure 2:
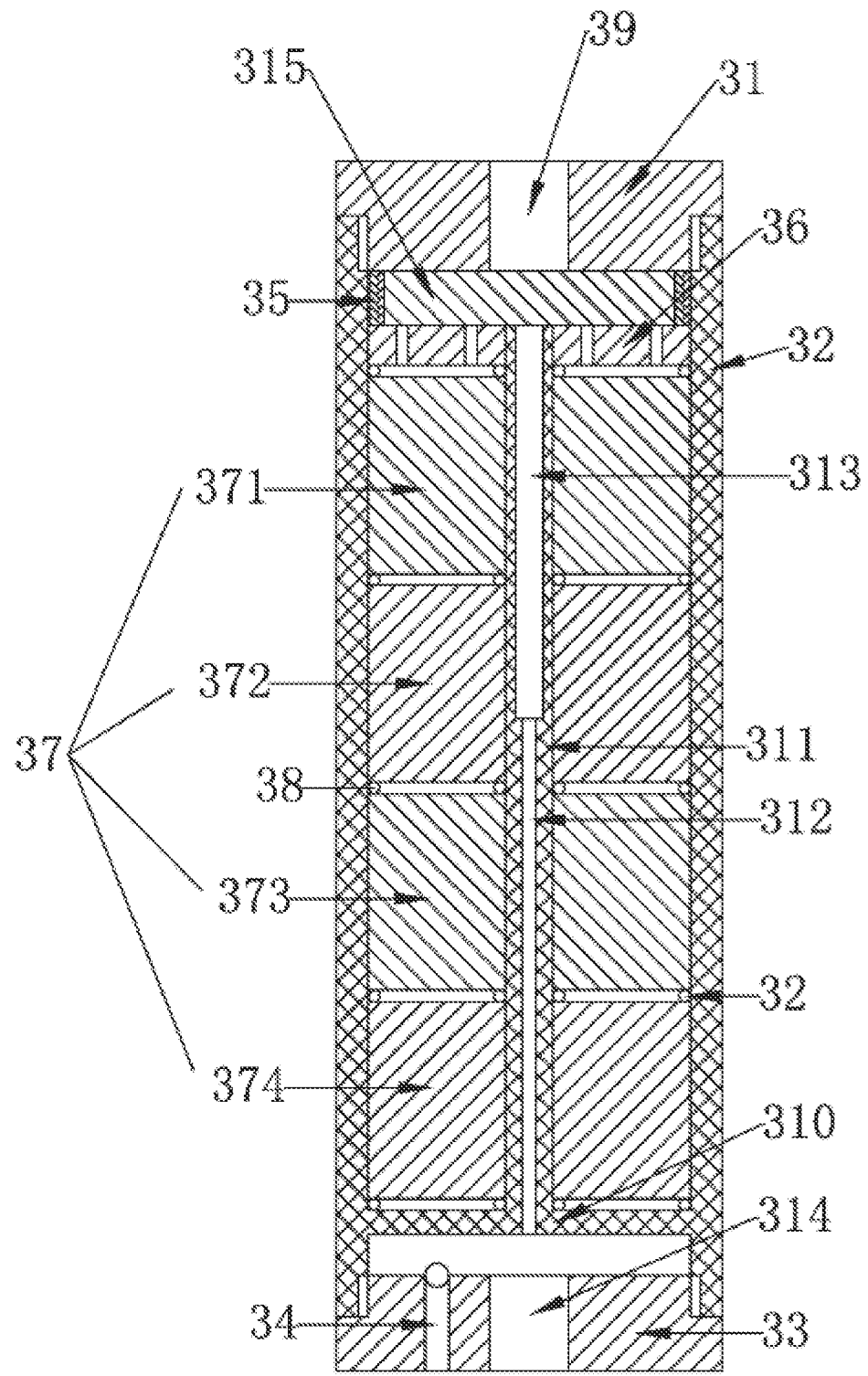
FIG. 2 is a cross-sectional view of a structure of a gas diluting and sampling connector according to the disclosure.
Figure 3:
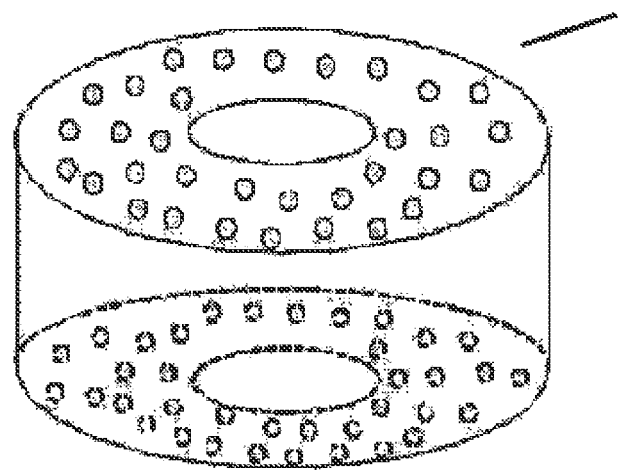
FIG. 3 is a diagram of a structure of a first filtration module according to the disclosure.
Figure 4:
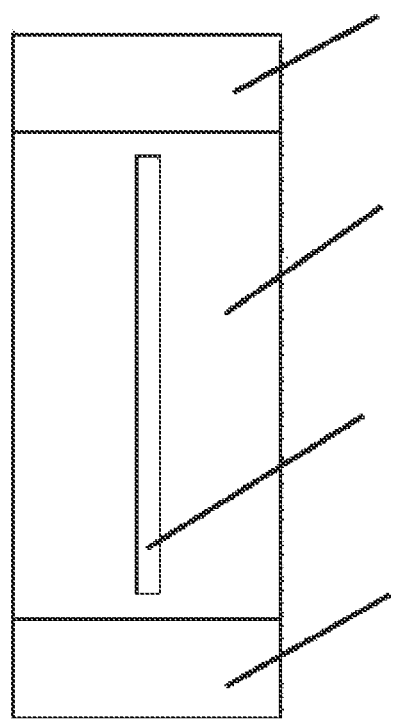
FIG. 4 is a diagram of an external structure of a gas diluting and sampling connector according to the disclosure.
Figure 5:
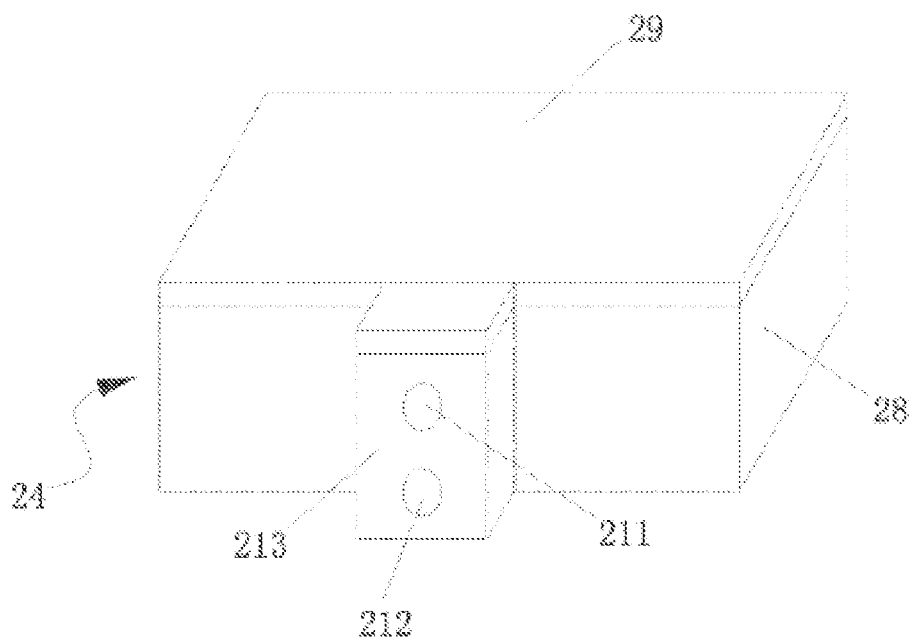
FIG. 5 is a diagram of an appearance of a sensor integrated module according to the disclosure.
Figure 6:
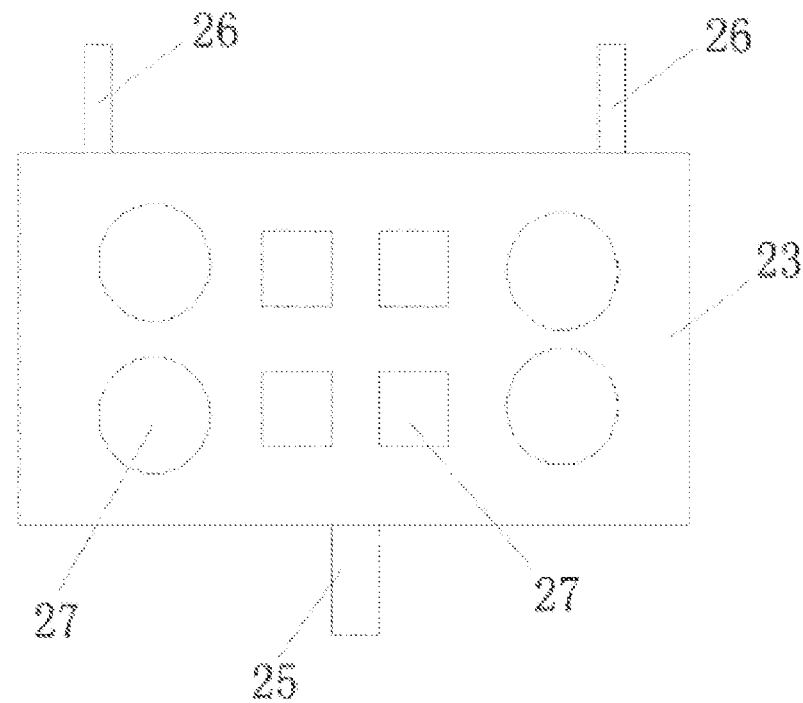
FIG. 6 is a diagram of a gas circuit communication mechanism of a sensor integrated module according to the disclosure.
Figure 7:
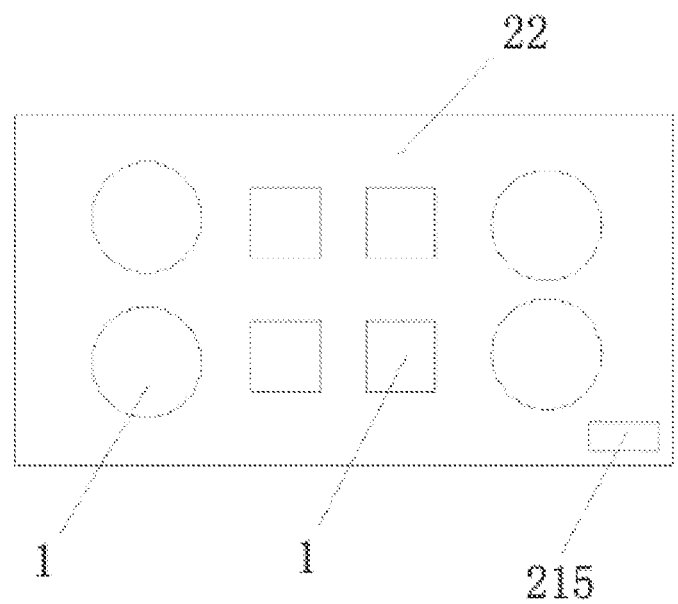
FIG. 7 is a diagram of a circuit board of an electrochemical sensor integrated in a sensor integrated module according to the disclosure.
Figure 8:
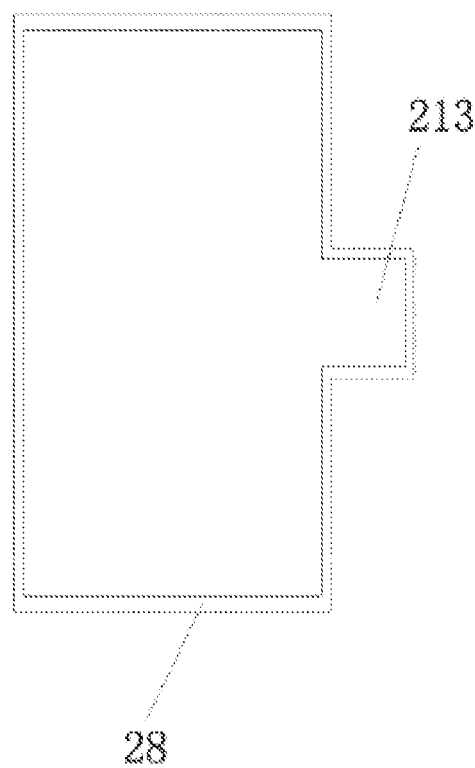
FIG. 8 is a top view of a sensor integrated module box body according to the disclosure.
Figure 9:
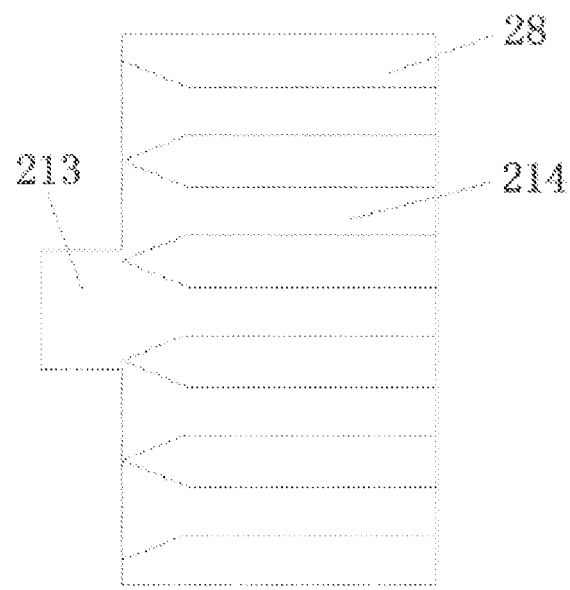
FIG. 9 is a bottom view of a sensor integrated module box body according to the disclosure.
Figure 10:
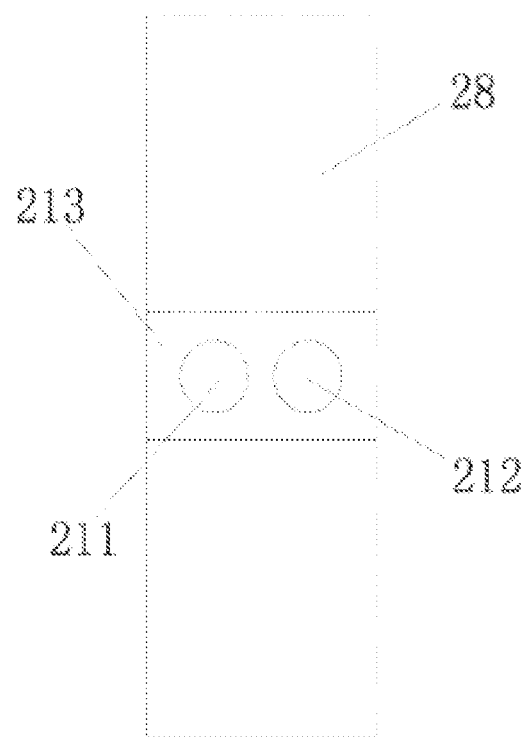
FIG. 10 is a side view of a sensor integrated module box body (including a plug-in protrusion side).
Figure 11:
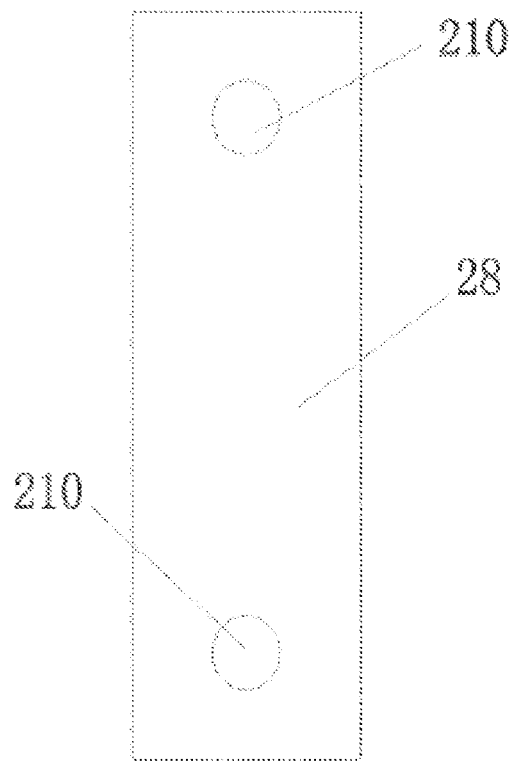
FIG. 11 is a view of another side of a sensor integrated module box body (the opposite side of the plug-in protrusion).
Figure 12:
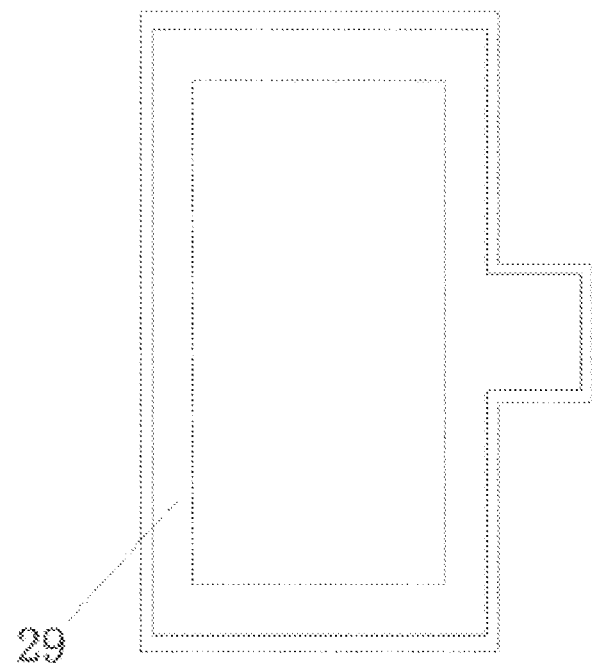
FIG. 12 is a view of a cover body of a sensor integrated module according to the disclosure.

As show in FIGS. 2-4, the gas diluting and sampling connector 3 of the disclosure includes a shell 32 being of a tubular structure, a front cover 31 and a rear cover 32 connected with the top and the bottom of the shell 32 through screw threads, a gas inlet 39 formed on the front cover 31, a gas outlet 314 formed on the rear cover 33, a sampling column 311 disposed in the shell 32 and coaxial to the shell 32, a filtration module 37 disposed around the outside of the sampling column 311 and used for forming clean air, a first porous barrier 36 detachably disposed at the upper inside of the shell 32 and used for dividing a sampling gas to the sampling column 311 and the filtration module 37, a porous fiber column 313 disposed on the upper part of the sampling column 311 and used for filtering fine particles in the sampling gas, a sample gas sampling hole 312 formed on the lower part of the sampling column 311 and connected with the porous fiber column 313, and a second porous barrier 310 disposed at the lower inside of the shell 32 and used for conducting the sampling gas and clean air, and the gas outlet 314 is connected with the sensor integrated module 2 through the pipeline; a cavity formed by the front cover 31 and the first porous barrier 36 is provided with a pre-filtration module 315 for filtering dust and oil particles in a sampling gas, the pre-filtration module 315 is a sintered Polypropylene fiber filtration core, a pressure spring 35 is disposed between the front cover 31 and the first porous barrier 316, and the pressure spring 35 is located in an interspace formed between the pre-filtration module 315 and the inner side of the shell 32.

A cavity formed by the second porous barrier 310 and the rear cover 33 is provided with a pressure sensoR 34 for, detecting the operation condition of the gas diluting and sampling connector, the filtration module 37 includes a first filtration module 371, a second filtration module 372, a third filtration module 373 and a fourth filtration module 374 which are disposed in sequence from top to bottom and in seal connection through an O-shaped rings 38, the first filtration module 371 is filled with a mixture of a potassium permanganate active alumina column and basic coaly activated carbon, the second filtration module 372 is filled with a refined filtration core made of non-woven paper, the third filtration module 373 is filled with palladium catalyzed aluminum oxide particles and the fourth filtration module 374 is filled with cocoanut active charcoal particles having a high iodine value; the first filtration module 371 is a ring-shaped box body, and the upper end surface and the lower end surface of the box body are of porous structures, the structures of the second filtration module 372, the third filtration module 373 and the fourth filtration module 374 are the same as that of the first filtration module 371; the shell 32 is made of a transparent material, or is provided with a transparent observation zone 316.

A method for using the gas diluting and sampling connector includes the following steps:

Step A: allowing a sample gas to enter into the inside of the shell via a gas inlet, where the sample gas is filtered with dust and oil particles through the pre-filtration module, and the sample gas is divided into two parts after passing through the first porous barrier, wherein one part of which flows into the filtration modules, and the other part of which flows into a sampling column;

Step B: the sample gas forms the clean air after multi-stage filtration in the filtration module (37), and the formed clean air enters the cavity formed by the second porous barrier and the rear cover;

Step C: the sample gas entering into the sampling column is filtered with fine particles in the porous fiber column, and finally enters into the cavity formed by the second porous barrier and the rear cover via a sample gas sampling hole; and Step D: in this cavity, the clean air is mixed with the sample gas by a certain dilution proportion and finally the diluted sample gas are discharged through the gas outlet, wherein the dilution proportion is determined based on the size of the sample gas sampling hole to achieve the purpose of diluting the sample gas.

The gas diluting and sampling connector 3 of the disclosure integrates a gas dilution functions on the sampling connector. After entering the inside of the sampling connector, one part of the sampling gas is purified into clean air through the filtration and, cleaning module, and the other part of the sampling gas passes through the porous fiber column and sample gas sampling hole so that the discharge amount of the sampling gas is controlled, and finally, air is mixed with the sampling gas in a certain proportion to achieve the purpose of diluting the sampling gas and facilitate subsequent gas detection. The gas diluting and sampling connector of the disclosure is mainly directed to sampling requirements in a high-concentration pollution gas, environment, and the sampling gas is directly diluted in a fixed proportion, which improves the convenience of use, and does not need additionally added accessories to reduce cost. And the sampling connector is simple in structure and small in volume.

In order to facilitate observation of use situations of a filter material filled in the filtration module 7, the shell 2 is made of a transparent material, or a transparent observation zone is disposed on the shell 2 so as to timely know the use situations of the filter material which can be conveniently and timely maintained and changed. Since the first porous barrier 6 can be detachably connected inside the shell 2, the filter material can be changed after the first porous barrier 6, which is convenient and quick. When the pressure spring disposed on the gas diluting and sampling connector 3 is connected with the shell through screw threads on the front cover, the first porous barrier can be extruded downwardly so that various filtration modules are closely contacted and then purposes of compressing and sealing the filtration modules in combination with the effect of the O-shaped ring. The pressure sensor disposed on the gas diluting and sampling connector 3 is used for detecting the pressure of the gas in the cavity and timely knowing the working situations of the connector to prevent the blocking of the inside of the connector.

As shown in FIGS. 5-12, the sensor integration module 2 includes a circuit board 22 integrated with eight electrochemical sensors 1, a gas circuit communication mechanism 23 and a sealing gas measurement box 24, wherein the circuit board 22 is integrated with eight automatic identification and failure detection circuits of the electrochemical sensors 1 which are in one-to-one correspondence to the eight electrochemical sensors 1, and each of the electrochemical sensors 1 is respectively accessed into the automatic identification and failure detection circuit of the corresponding electrochemical sensor; the gas circuit communication mechanism 23 is provided with a gas inlet pipe 25, two gas outlet pipes 26 and eight unitary gas chambers 27, wherein the gas inlet pipe 25 is respectively communicated with eight unitary gas chambers 27 through pipelines, each of the gas outlet pipes 27 is respectively communicated with four unitary gas chambers 27, the eight gas unitary gas chambers 27 respectively correspond to the eight electrochemical sensors 1, the circuit board 22 is sealed and covered on the gas circuit communication mechanism 23, and each of the electrochemical sensors 1 is respectively located inside the corresponding the unitary gas chamber 27; the gas measurement box 24 includes a box body 28 and a cover body 29 covering the box body 28, the gas circuit communication mechanism 23 in which the circuit board 22 is sealed and covered is disposed in the box body 28, the box body 28 is provided with a gas inlet pipe hole 212 corresponding to the gas inlet pipe 25 and a gas outlet pipe hole 210 corresponding to the gas outlet pipe 26, the box body 28 is provided with a plug wire hole 211, the circuit board 22 is provided with a wire plug wire end 215 respectively connected with the eight automatic identification and failure detection circuits of the electrochemical sensors, the plug wire end 215 penetrates through the plug wire hole 211 to be connected with eight ADC circuits 4, each of the ADC circuits 4 is respectively connected with one of the automatic identification and failure detection circuits of the electrochemical sensors through the plug wire end 215, and the gas inlet pipe 25 penetrates through the gas outlet hole 210 to be communicated with the gas outlet hole 314.

The circuit board 22 is fixedly connected with the gas circuit communication mechanism 23 through bolts, a silica gel seal ring is disposed between the gas circuit communication mechanism 23 and the circuit board 22, and the circuit board 22 and the gas circuit communication mechanism 23 are sealed through the silica gel seal ring, and the gas circuit communication mechanism 23, the box body 28 and the cover body 29 are all made of resins; one side of the box body 28 is provided with a plug-in protrusion 213, and the gas inlet pipe hole 212 and the plug wire hole 211 are both provided with the plug-in protrusions, the plug wire end 215 is located at the plug-in protrusion 213, the bottom surface of the box body 28 is provided with a plug-in dovetail groove 214, the gas detector body is provided with a socket plug-in dovetail groove matched with the plug-in dovetail groove 214, the sealing gas measurement box 24 is plugged into the gas detector body through the plug-in dovetail groove 214, the gas detector body is provided with a plug-in port, and the gas outlet 314 and all the ADC circuits 4 are located in the plug-in port; when the sealing gas measurement box 24 is plugged onto the gas detector body, the plug-in protrusion 213 is inserted into the plug-in port, and the automatic identification and failure detection circuits of the eight electrochemical sensors are respectively connected with the eight ADC circuits 4 through the plug wire end 215, the automatic identification and failure detection circuits of the electrochemical sensors are also connected with the MCU singlechip 5 through the plug wire end 215, and the gas inlet pipe 25 is Communicated with the gas outlet 314.

The sensor integrated module is simple in structure, scientific and reasonable and convenient to use, can integrate eight electrochemical sensors which can simultaneously detect gases and do not generate crosstalk, and meanwhile also can be conveniently inserted on the wide-concentration multi-component detector, thereby effectively improving the gas detection efficiency of the wide-concentration multi-component detector and gaining precious time for rescue and relief work.

The disclosure includes electrochemical sensors, a circuit board and a gas circuit communication mechanism, the circuit board is integrated with eight electrochemical sensors and automatic identification and failure detection circuits of the electrochemical sensors, each of the automatic identification and failure detection circuits of the electrochemical sensors is connected with one electrochemical sensor, the circuit board is sealed and covered on the gas circuit communication mechanism, each electromechanical sensor is placed in one unitary gas chamber, the gas inlet pipe is respectively communicated with each unitary gas chamber, each output pipe is respectively communicated with four unitary gas chambers, in such a way, the gas inlet pipe is communicated with a sampling pipe on the wide-concentration multi-component hazardous gas detector, the sampling pipe on the wide-concentration multi-component hazardous gas detector samples a gas leaked from a hazardous product and then enters the gas inlet pipe via the sampling pipe, subsequently enters into eight unitary gas chambers and finally discharged from the gas outlet pipe. When the gas enters the unitary gas chamber, a corresponding electrochemical sensor can detect it. Since eight unitary gas chambers are distributed in a parallel manner, eight electrochemical sensors located in eight unitary gas chambers do not mutually generate crosstalk when in working with high detection precise; since each electrochemical sensor is separately accessed to one automatic identification and failure detection circuits of the electrochemical sensors, it can respectively independently work, namely, can simultaneously detect, eight hazardous gases, and therefore detection efficiency is high, and precious time, for rescue and relief work can be gained.

The circuit board is fixed on the gas circuit communication mechanism through bolts and sealed through the silica seal ring. The circuit board and the gas circuit communication mechanism are detachable, and therefore convenient to overhaul. The sealing gas measurement box is provided with the plug-in protrusion and the plug-in dovetail groove, and the plug-in dovetail groove can conveniently fix the sealing gas measurement box to the wide-concentration multi-component hazardous gas detector. The plug-in protrusion is opposite to the plug-in port of the wide-concentration multi-component hazardous gas detector, so that the plug wire end can be connected with a control element, the gas inlet pipe can be communicated with the sampling pipe and therefore installation is convenient, and detection efficiency can be improved.

Figure 13:
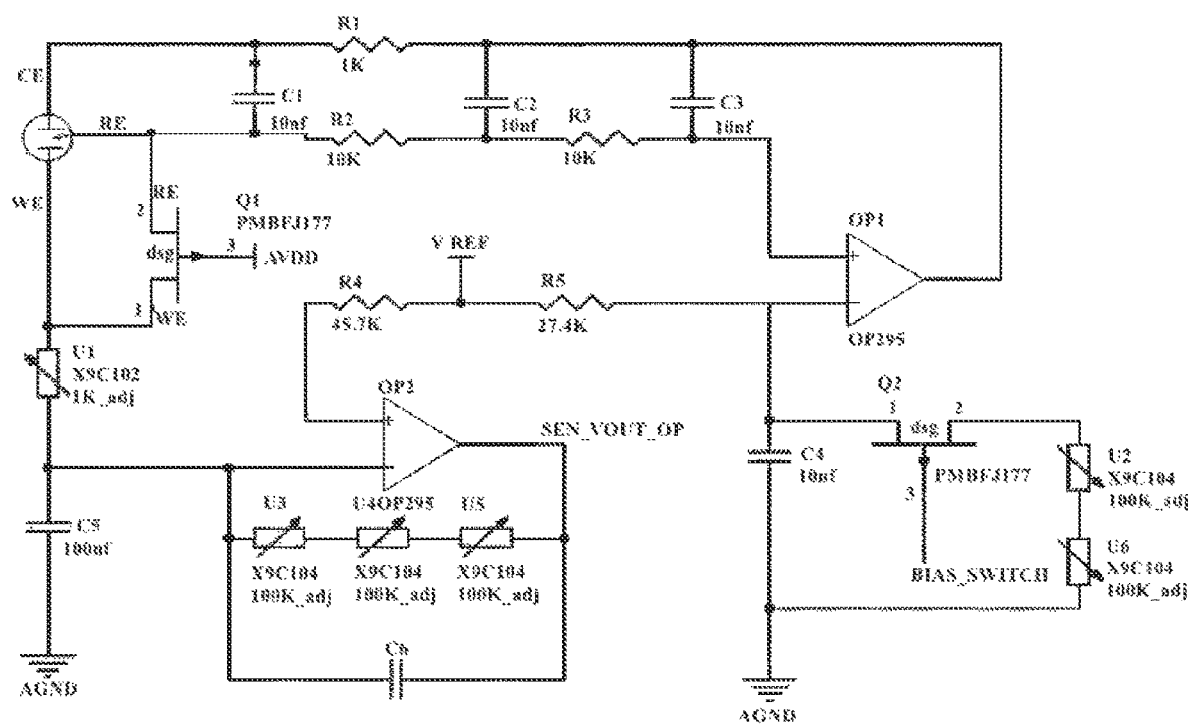
FIG. 13 is a driving principle diagram of an automatic identification and failure detection circuit for an electrochemical sensor automatic identification and failure detection circuit according to the disclosure.

As shown in FIG. 13, the automatic identification and failure detection circuits of the eight electrochemical sensors are configured to automatically identify the electrochemical sensors and perform failure detection on the identified electrochemical sensors; the automatic identification and failure detection circuit of the eight electrochemical sensor includes an electrochemical sensor access end provided with a CE pin access end, a RE pin access end and a WE pin access end, a programmable and adjustable resistor U1, a MOS transistor Q1, a resistor R1, a resistor R2, a resistor R3, a resistor R4, a resistor R5, a capacitor C1, a capacitor C2, a capacitor C3, a capacitor C5, an amplifier OP1, an automatic gain adjustment circuit and an automatic bias generating circuit, wherein the CE access end, the RE access end and the WE access end are respectively configured to couple a CE pin, a RE pin and a WE pin of the electrochemical sensor; three pins of the electrochemical sensor are respectively connected with the CE pin access end, the RE pin access end and the WE pin access end.

The CE pin access end, the resistor R1 and an output terminal of the amplifier OP1 are successively connected in series, the RE pin access end, the resistor R2, the resistor R3 and the noninventing input terminal of the amplifier OP1 are successively connected in series, the WE pin access end, the programmable and adjustable resistor U1, the automatic gain adjustment circuit, the resistor R4, the resistor R5 and the inverting input terminal of the amplifier OP1 are successively connected in series; both ends of the capacitor C1 are respectively connected with the CE pin access end and the RE pin access end, both ends of the capacitor C3 are respectively connected with the noninventing input terminal of the amplifier OP1 and the RE pin access end and the output terminal of the amplifier OP1; one end of the capacitor C5 is connected with the programmable and adjustable U1, the other end of the capacitor C5 is in ground connection; one end of the capacitor C2 is connected between the resistor R2 and the resistor R3, and the other end of the capacitor C2 is connected between the resistor R1 and the output terminal of the amplifier OP1.

The automatic bias generating circuit is connected with the inverting input terminal of the amplifier OP1 and is also in ground connection, the drain electrode D of the MOS transistor Q1 is connected with the WE pin access end, the source electrode S of the MOS transistor Q1 is connected with the RE pin access end, the gate electrode G of the MOS Q1 and the automatic bias generating circuit are respectively connected with one pin of the MCU singlechip, one pin of the MCU singlechip is connected between the resistor R4 and the resistor R5, and the automatic gain adjustment circuit is connected with the MCU singlechip through the ADC circuit; the automatic gain adjustment circuit includes an amplifier OP2, a programmable and adjustable resistor U3, a programmable and adjustable resistor U4, a programmable and adjustable resistor U5 and a capacitor C6, wherein the inverting input terminal of the amplifier OP2, the programmable and adjustable resistor U3, the programmable and adjustable resistor U4, the programmable and adjustable resistor U5 and the output terminal of the amplifier OP2 are connected in series, both ends of the capacitor C6 are respectively connected with the inverting input, terminal of the amplifier OP2 and the output terminal of the amplifier OP2, the inverting input terminal of the amplifier OP2 is connected with the programmable and adjustable resistor U1, the noninventing input terminal of the amplifier OP2 is connected with the resistor R4, the output terminal of the amplifier OP2 is connected with the MCU singlechip through the ADC circuit.

The automatic bias generating circuit comprises an MOS transistor Q2, programmable and adjustable resistor U2, a programmable and adjustable resistor U6 and a capacitor C4, wherein the drain electrode D of the MOS transistor Q2, the capacitor C4, the programmable and adjustable resistor U6, the programmable and adjustable resistor U2 and the source electrode S of the MOS transistor Q2 are successively connected in series, the drain electrode D of the MOS transistor Q2 is connected with the inverting input terminal of the amplifier OP1, the gate electrode G of the MOS transistor Q2 is connected with one pin of the MCU singlechip, and the capacitor C4 and the programmable and adjustable resistor U6 are in ground connection; the programmable and adjustable resistor U1 is an X9C102 programmable resistor with a resistance value adjustable range of 0-1 KΩ, the programmable and adjustable resistor U2, the programmable and adjustable resistor U3, the programmable and adjustable resistor U4, the programmable and adjustable resistor U5 and the programmable and adjustable resistor U6 are all X9C104 programmable resistors with a resistance value adjustable range of 0-100 KΩ;

the resistance value of the resistor R1 is 1 KΩ the resistance value of the resistor R2 is 10 KΩ the resistance value of the resistor R3 is 10 KΩ the resistance value of the resistor R4 is 47.5 KΩ and the resistance value of the resistor R5 is 27.4 KΩ; the capacitor C1 is a 10 nf capacitor, the capacitor C2 is a 10 nf capacitor, the capacitor C3 is a 10 nf capacitor, the capacitor C4 is a 10 nf capacitor, and the capacitor C5 is a 100 nf capacitor.

The programmable and adjustable resistors U1-6 are all X9Cxxx series programmable and adjustable resistors, which can adjust the particular resistance value of the resistor through the MCU singlechip.

The programmable and adjustable resistors U1 is X9C102, which can generate a resistance value of 0-1K and can meet the needs for all the electrochemical sensor loading resistors, thus this circuit can fit to all the commercially available electrochemical sensors. When different brands of electrochemical sensors are inserted into the circuit, the MCU singlechip can adjust the loading resistor according to parameters of different electrochemical sensors.

The programmable and adjustable resistors U3/U4/U5 in the automatic gain adjustment circuit are connected in series by adopting X9C104 programmable and adjustable resistors, the MCU singlechip can automatically adjust three resistors according to the need of the system so as to achieve the purpose of automatic gain adjustment, in such a way, the gain can be adjusted according to a response result. When the output current of the sensor is relatively small to lead to a fact that the output of the SEN_VOUT_OP cannot be measured due to too small, the MCU singlechip can properly adjust the values of U3/U4/U5 to increase the gain; when the output current of the sensor is relatively large to lead to a fact that the output of the SEN_VOUT_OP exceeds a scale due to too large, the MCU singlechip can properly adjust the values of U3/U4/U5 to diminish the gain, and therefore is matched with the measurement scale of the later-grade AD circuit;

For the automatic bias generating circuit, when bias needs to be generated to achieve the sensor detection function or some sensors themselves need to generate bias, the MCU singlechip can allow the bias circuit U2/U6 to generate the needed bias by lowering the BIAS SWITCH pin of Q2, U2/U6 is connected in series by adopting X9C104 programmable and adjustable resistors, and the MCU singlechip can automatically adjust two resistors according to the need of the system, thereby achieving the purpose of bias adjustment.

The automatic identification and failure detection circuit is simple in structure, scientific and reasonable in design and convenient to use, can quickly, efficiently, precisely and automatically identify the electrochemical sensors, and quickly, efficiently and precisely detect whether the electrochemical sensors failed.

A method for performing automatic identification on an electrochemical sensor using the automatic identification and failure detection circuit for the electrochemical sensor comprises the following steps:

Step ①: storing official information of electrochemical sensor for fire protection in a storage, and establishing an electrochemical sensor database;

Step ②: detecting a no-load output value of a to-be-identified electrochemical sensor in an actual system and a characteristic value of an output curve during a power-on process through manual test of the to-be-identified electrochemical sensor, and recording the tested no-load output value and the characteristic value into the storage;

Step ③: accessing the to-be-identified electrochemical sensor into the automatic identification and failure detection circuits of the electrochemical sensors, powering on the MCU singlechip, and the MCU singlechip reads the no-load output value and the characteristic value of the to-be-identified electrochemical sensor from the storage;

Step ④: the MCU singlechip respectively performs correct configuration on the automatic identification and failure detection circuits of the electrochemical sensors according to the no-load output value and the characteristic value of the to-be-identified electrochemical sensor; and Step ⑤: the MCU singlechip identifies the power-on of the to-be-identified electrochemical sensor through the automatic identification and failure detection circuit of the electrochemical sensor, and monitors the voltage values of the to-be-identified electrochemical sensor at each period of time during the power-on process through the ADC circuit, and meanwhile matching the monitored voltage values with the electrochemical sensors in the electrochemical sensor database in the storage, thereby automatically identifying the to-be-identified electrochemical sensor.

The automatic identification and failure detection circuits of the electrochemical sensors can automatically identify the electrochemical sensors, is simple in identification process, scientific and reasonable in design and convenient to use, can precisely and automatically identify the electrochemical sensors, is applicable to wide electrochemical sensor variety range and high in identification efficiency.

A method for performing failure detection on an electrochemical sensor using the automatic identification and failure detection circuits for the electrochemical sensors comprises the following steps:

Step I: accessing the to-be-identified electrochemical sensor into an automatic identification and failure detection system of the electrochemical sensor, and starting the automatic identification and failure detection system of the electrochemical sensor;

Step II: initializing the automatic identification, and failure detection system of the electrochemical sensor;

Step III: changing the parameters of the automatic identification and failure detection system of the electrochemical sensor s to allow a generation of ±1 mv perturbance in a bias of the to-be-detected electrochemical sensor;

Step IV: detecting whether the output voltage of the automatic identification and failure detection system of the electrochemical sensor changes with the perturbance in the bias of the to-be-detected electrochemical sensor, wherein if the output voltage has a large perturbance amplitude, the to-be-detected electrochemical sensor is detected as normal; if the output voltage has a small perturbance amplitude, the to-be-detected electrochemical sensor is detected as failure.

According to the disclosure, the automatic identification and failure detection system of the electrochemical sensor inputs a bias of ±1 mv, the singlechip is connected with the voltage output terminal of the automatic identification and failure detection circuits of the electrochemical sensors so as to monitor $V_{out}$ change in the automatic identification and failure detection circuits of the electrochemical sensors. When the $V_{out}$ changes and a correct bias is input, the output voltage $V_{out}$ from the automatic identification and failure detection circuits of the electrochemical sensors returns to normal. Accordingly, whether the sensor is normal can be determined.

If the bias of ±1 mv is input and the output $V_{out}$ of the automatic identification and failure detection circuits of the electrochemical sensors does not change, it is initially determined that the electrochemical sensor is failed. If the bias is changed into a correct value to be input and the automatic identification and failure detection circuits of the electrochemical sensors still has no normal output, it is determined that the electrochemical sensor is damaged, and the detection result is quick, efficient and precise.

An implementation method of a wide-concentration multi-component hazardous gas detector includes the following steps:

Step 1: selecting an appropriate sensor module according to situations of an accident site, and starting a host;

Step 2: starting an automatic identification and failure detection circuit for an electrochemical sensor to automatically identify the electrochemical sensor, whereby a automatic identification and failure detection system automatically determines the sensor module in use and a working state thereof by the system;

Step 3: performing effectiveness detection of the electrochemical sensor using the automatic identification and failure detection circuit for the electrochemical sensor, selecting an electrochemical sensor capable of normal operation, and connecting unitary gas chambers equipped with the electrochemical sensors to form a passage;

Step 4: placing a gas diluting and sampling connector in a to-be-detected hazardous gas, and meanwhile starting a small evacuation pump to pump the diluted hazardous gas into the passage of the sensor integrated module;

Step 5: an MCU singlechip respectively performs sampling after an MCU singlechip by starting the electrochemical sensor, sampling in the passage every 1 second, performs electrochemical sensor cross sensitivity calculating and processing on the electrochemical sensor on data obtained by sampling, wherein the results are displayed in real time through an LED display module, and meanwhile the calculated and processed date is stored through a SI) card data storage module.

The MCU singlechip starts eight gas path sampling circuits for sampling, data obtained by sampling is subjected to operation processing in the master controller, the result after operation is fed to a display screen for real-time display and meanwhile deliver the operated data to an external storage for data storage. The display screen adopts an industrial serial port screen, a human-computer interface independently operates on the circuit of the display screen, the operation information of the human-computer interface is transmitted to the maser controller through the serial port, and the master controller adjusts relevant work states. Portable equipment has a function of usb mass storage, and after the computer is connected by a user, relevant operations of memorized data files are processed with a conventional U disc processing manner.

The cross sensitivity operation method of the electrochemical sensor of the disclosure includes:

1. It is assumed that all the electrochemical sensors have linear response to gases and do not generate system noises, a signal of a gas x on an x sensor is as follows: $C_{x\ detection} = k_x C_x$, $k_x$ is response of the X sensor on the x gas:

$$\begin{bmatrix} C_{1\ determined} \\ C_{2\ determined} \\ C_{3\ determined} \\ C_{4\ determined} \\ C_{5\ determined} \end{bmatrix} = \begin{bmatrix} k_{11} & k_{12} & k_{13} & k_{14} & k_{15} \\ k_{21} & k_{22} & k_{23} & k_{24} & k_{25} \\ k_{31} & k_{32} & k_{33} & k_{34} & k_{35} \\ k_{41} & k_{42} & k_{43} & k_{44} & k_{45} \\ k_{51} & k_{52} & k_{53} & k_{54} & k_{55} \end{bmatrix} \begin{bmatrix} C_1 \\ C_2 \\ C_3 \\ C_4 \\ C_5 \end{bmatrix}$$

2. An equation is obtained according to the k value calculated in an EXCEL file $$C_{CO\ determined} = C_{CO} + 0.2 C_{NO};$$

$$C_{HCl\ determined} = C_{HCl} + 4 C_{H2S} + 2 C_{SO2} + 2.25 C_{NO};$$

$$C_{HCN\ determined} = C_{HCN} + 2 C_{H2S} + 0.3 C_{SO2};$$

$$C_{SO2\ determined} = C_{SO2};$$

$$C_{C6H6\ determined} = C_{benzene} + 1.105 C_{CO} + 4.66 C_{H2S} + 1.25 C_{SO2}$$

Since concentrations of $H_2S$, NO and $NO_2$ gases are not monitored, the concentrations of $H_2S$, MO and $NO_2$ gases in a mixed gas is temporarily set as 0. Accordingly, actual concentrations of various components in an exhaust gas according to measured concentrations.

$$C_{CO} = C_{CO\ determined};$$

$$C_{HCl} = C_{HCl\ determined} - 2 C_{SO2\ determined};$$

$$C_{HCN} = C_{HCN\ determined} - 0.3 C_{SO2\ determined};$$

$$C_{SO2} = C_{SO2\ determined};$$

$$C_{C6H6} = C_{C6H6\ determined} - 1.105 C_{CO\ determined} - 1.25 C_{SO2\ determined}$$

Since $H_2S$, NO and $NO_2$ have great influence on other electrochemical gas sensors, it is suggested to add $H_2S$, NO and $NO_2$ sensors in order to get more accurate results.

The disclosure has the following technical features:

Multi-component detection—8 gases can be detected simultaneously.

Wide-concentration detection—detectable concentration range is wide.

Anti-interference detection—interference between gas sensors is eliminated so that the gas can be precisely qualified and quantified.

Hazardous gases—such as CN, HCl, $SO_2$, $NO_2$, CO, NO and $H_2S$

Portability—weight is ≤3 Kg, all the instruments are integrated together, so volume is small, and weight is light.

The disclosure adopts a gas on-line dilution technology to dilute a high-concentration sample gas into a low-concentration gas in a proportion and then introduce the low-concentration gas into a gas sensor for measurement.

The disclosure adopts a sensor array technology and sensor automatic identification technology, designs a plug-in sensor module and expands test kinds. Because the sensor has a cross sensitivity defect, that is, the same sensor responds to different gases, responses to other gases are eliminated by expanding gas test kinds, so as to solve false positive and false, negative problems.

The disclosure adopts an electronic nose pattern recognition, algorithm (cross sensitivity calculation algorithm of electrochemical gas sensors) adds or subtracts the signal measured by each sensor to reduce the influence of cross sensitivity between sensors on gas concentration measurement.

The above-mentioned embodiments are only one of preferred embodiments of the disclosure and should not be used to limit the scope of protection of the disclosure. The technical problems solved by any meaningless changes or embellishments made in the main design idea and spirit of, the disclosure are still consistent with those of the disclosure, and should be included in the scope of protection of the disclosure.

We claim:

1. A wide-concentration multi-component hazardous gas detector, comprising a gas detector body, a gas diluting and sampling connector (3) disposed in the gas detector body for diluting the concentration of a to-be-detected gas to enlarge the gas concentration detection range to avoid the poisoning and failure of a sensor, a sensor integrated module (2) plugged-in on the gas detector body and in pipeline connection with the gas diluting and sampling connector (3) and used for integrating a multiple electrochemical sensor (1) without mutual inter-crosstalk so as to perform gas detection, a ADC circuit (4) disposed within the gas detector body in the same amount with the electrochemical sensors (1) and respectively connected with the sensor integrated module (2), an MCU singlechip (5) disposed within the gas detector body and respectively connected with the ADC circuit (4) through a SPI bus, a acousto-optic alarm (6), a 4-button keyboard module (7) and an LED display module (8) disposed on the gas detector body and respectively connected with the MCU singlechip (5), an SD card data storage module (9) disposed within the gas detector body and exchanging data with the MCU singlechip (5), a lithium battery pack (11) disposed within the gas detector body and connected with the MCU singlechip (5) through power supply control and an electric quantity display module (10), and a remote command platform signal collection terminal (14);

a small evacuation pump (12) connected with the MCU singlechip (5) is disposed on a pipeline where the gas diluting and sampling connector (3) is connected with the sensor integrated module (2), the MCU singlechip (5) is in wireless connection with the remote command platform signal collection terminal (14) through a 433 Mhz signal transmission module (13), and the MCU singlechip (5) is connected with the sensor integrated module (2), the gas diluting and sampling connector (3) comprises a shell (32) present as a tubular structure, a front cover (31) and a rear cover (33) connected with the top and the bottom of the shell (32) through screw threads, a gas inlet (39) formed on the front cover (31), a gas outlet (314) formed on the rear cover (33), a sampling column (311) disposed in the inside of the shell (32) and coaxial to the shell (32), a filtration module (37) disposed around the outside of the sampling column (311) and used for forming clean air, a first porous barrier (36) detachably disposed at the upper inside of the shell (32) and used for shunting a sampling gas to the sampling column (311) and the filtration module (37), a porous fiber column (313) disposed on the upper part of the sampling column (313) and used for filtering particles in the sampling gas, a sample gas sampling hole (312) formed on the lower part of the sampling column (311) and connected with the porous fiber column (313), a second porous barrier (310) disposed at the lower inside of the shell (32) and used for conducting the sampling gas and the clean air, and the gas outlet (314) is connected with the sensor integrated module (2) through the pipeline;

a cavity formed by the front cover (31) and the first porous barrier (36) is provided with a pre-filtration module (315), the pre-filtration module (315) is a sintered Polypropylene fiber filtration core and used for filtering dust and oil particles in the sampling gas, a pressure spring (35) is disposed between the front cover (31) and the first porous barrier (36), and the pressure spring (35) is located in an interspace formed between the pre-filtration module (315) and the inner side wall of the shell (32).

2. The wide-concentration multi-component hazardous gas detector according to claim 1, wherein a cavity formed by the second porous barrier (310) and the rear cover (33) is provided with a pressure sensor (34) for detecting the operation condition of the gas diluting and sampling connector (3), the filtration module (37) comprises a first filtration module (371), a second filtration module (372), a third filtration module (373) and a fourth filtration module (374) which are disposed in sequence from top to bottom and in seal connection through an O-shaped rings (38), the first filtration module (371) is filled with a mixture of a potassium permanganate active alumina column and alkalic coaly activated carbon, the second filtration module (372) is filled with a refined filtration core made of non-woven paper, the third filtration module (373) is filled with palladium catalyzed aluminum oxide particles and the fourth filtration module (374) is filled with cocoanut active charcoal particles having a high iodine value;

the first filtration module (371) is a ring-shaped box body, and the upper end surface and the lower end surface of the box body are of a porous structure, structures of the second filtration module (372), the third filtration module (373) and the fourth filtration module (374) are the same with that of the first filtration module (371); the shell (32) is made of a transparent material, or is provided with a transparent observation zone (316).

3. The wide-concentration multi-component hazardous gas detector according to claim 2, wherein a method for using the gas diluting and sampling connector (3) comprises the following steps:

Step A: allowing a sample gas to enter into the inside of the shell (32) via the gas inlet (39), where the sample gas is filtered with dust and oil particles through the pre-filtration module (315), and the sample gas is divided into two parts after passing through the first porous barrier (36), one part of which flows into the filtration module (37), and the other part of which flows into the sampling column (311);

Step B: the sample gas forms the clean air after multi-stage filtration in the filtration module (37), and the formed clean air enters the cavity formed by the second porous barrier (310) and the rear cover (33);

Step C: meanwhile particles in the sample gas entering into the sampling column (311) is filtered with particles in the porous fiber column (313), and finally enters into the cavity formed by the second porous barrier (310) and the rear cover (33) via the sample gas sampling hole (312); and Step D: in the cavity, the clean air is mixed with the sample gas by a certain dilution proportion and finally the diluted sample gas are discharged through the gas outlet (314), wherein the dilution proportion is determined based on a size of the sample gas sampling hole (312) to achieve the purpose of diluting the sampling gas.

4. The wide-concentration multi-component, hazardous gas detector according to claim 3, wherein the sensor integration module (2) comprises a circuit board (22) integrated with eight electrochemical sensors (1), a gas circuit communication mechanism (23) and a sealing gas measurement box (24), wherein the circuit board (22) is integrated with eight automatic identification and failure detection circuits of the electrochemical sensors (1) in one-to-one correspondence to the eight electrochemical sensors (1), each of the electrochemical sensors (1) is respectively accessed into the corresponding automatic identification and failure detection circuit of the electrochemical sensors (1):

the gas circuit communication mechanism (23) is provided with a gas inlet pipe (25), two gas outlet pipes (26) and eight unitary gas chambers (27), wherein the gas inlet pipe (25) is respectively communicated with the eight unitary gas chambers (27) through the pipeline, each of the gas outlet pipes (26) is respectively communicated with the four unitary gas chambers (27) through the pipeline, the eight unitary gas chambers (27) respectively correspond to the eight electrochemical sensors (1), the circuit board (22) is sealed and covered on the gas circuit communication mechanism (23), and each of the electrochemical sensors (1) is respectively located inside of the corresponding unitary gas chamber (27);

the sealing gas measurement box (24) comprises a box body (28) and a cover body (29) covering the box body (28), the gas circuit communication mechanism (23) sealed and covered by the circuit board (22) is disposed within the box body (28), the box body (28) is provided with a gas inlet pipe hole (212) corresponding to the gas inlet pipe (25) and a gas outlet pipe hole (210) corresponding to the gas outlet pipe (26), the box body (28) is provided with a plug wire hole (211), the circuit board (22) is provided with an plug wire end (215) respectively connected with the eight automatic identification and failure detection circuits of the electrochemical sensors (1), the plug wire end (215) penetrates through the plug wire hole (211) to be connected with the ADC circuit (4), the ADC circuit (4) is provided with eight, each of the ADC circuits (4) is respectively connected with one of the automatic identification and failure detection circuits of the electrochemical sensors (1) through the plug wire end (215), and the gas inlet pipe (25) penetrates through the gas outlet hole (210) to be communicated with the gas outlet hole (314).

5. The wide-concentration multi-component hazardous gas detector according to claim 4, wherein the circuit board (22) is fixedly connected with the gas circuit communication mechanism (23) through a bolt, a silica gel seal ring is disposed between the gas circuit communication mechanism (23) and the circuit board (22), and the circuit board (22) and the gas circuit communication mechanism (23) are sealed through the silica gel seal ring, and the gas circuit communication mechanism (23), the box body (28) and the cover body (29) are all made of resin;

one side of the box body (28) is provided with a plug-in protrusion (213), and the gas inlet pipe hole (212) and the plug wire hole (211) are both provided with the plug-in protrusions (213), the plug wire end (215) is located at the plug-in protrusion (213), the bottom surface of the box body (28) is provided with a plug-in dovetail groove (214), the gas detector body is provided with a socket dovetail groove matched with the plug-in dovetail groove (214), the sealing gas measurement box (24) is plugged in with the gas detector body through the plug-in dovetail groove (214), the gas detector body is provided with a plug-in port, the gas outlet (314) and all the ADC circuits (4) are located within the plug-in port, when the sealing gas measurement box (24) is plugged onto the gas detector body, the plug-in protrusion (213) is plugged into the plug-in port, and the eight automatic identification and failure detection circuits of the electrochemical sensors (1) are respectively connected with eight ADC circuits (4) through the plug wire end (215), the automatic identification and failure detection circuits of the eight electrochemical sensors (1) are also respectively connected with the MCU singlechip (5) through the plug wire end (215), and the gas inlet pipe (25) is communicated with the gas outlet (314).

6. The wide-concentration multi-component hazardous gas detector according to claim 5, wherein the automatic identification and failure detection circuits of the electrochemical sensors (1) are used to automatically identify the electrochemical sensors (1) and perform failure detection on the identified electrochemical sensors (1);

the automatic identification and failure detection circuits of the electrochemical sensors (1) comprises an electrochemical sensor access port provided with a CE pin access end, a RE pin access end and a WE pin access end, a programmable and adjustable resistor U1, an MOS transistor Q1, a resistor R1, a resistor R2, a resistor R3, a resistor R4, a resistor R5, a capacitor C1, a capacitor R2, a capacitor C3, a capacitor C5, an amplifier OP1, an automatic gain adjustment circuit and an automatic bias generating circuit, wherein the CE access end, the RE access end and the WE access end are respectively used to access a CE pin, a RE pin and a WE pin of the electrochemical sensor (1);

three pins of the electrochemical sensor (1) are respectively connected with the CE pin access end, the RE pin access end and the WE pin access end;

the CE pin access end, the resistor R1 and an output terminal of the amplifier OP1 are successively connected in series, the RE pin access end, the resistor R2, the resistor R3 and the noninverting input terminal of the amplifier OP1 are successively connected in series, the WE pin access end, the programmable and adjustable resistor U1, the automatic gain adjustment circuit, the resistor R4, the resistor R5 and the inverting input terminal of the amplifier OP1 are successively connected in series;

both ends of the capacitor C1 are respectively connected with the CE pin access end and the RE pin access end, and both ends of the capacitor C3 are respectively connected with the noninverting input terminal of the amplifier OP1 and the output terminal of the amplifier OP1; one end of the capacitor C5 is connected with the programmable and adjustable resistor U1, and the other end of the capacitor C5 is in ground connection; one end of the capacitor C2 is connected between the resistor R2 and the resistor R3, and the other end of the capacitor C2 is connected between the resistor R1 and the output terminal of the amplifier OP1;

the automatic bias generating circuit is connected with the inverting input terminal of the amplifier OP1 and is also in ground connection, a drain electrode D of the MOS transistor Q1 is connected with the WE pin access end, a source electrode S of the MOS transistor Q1 is connected with the RE pin access end, a gate electrode G of the MOS transistor Q1 and the automatic bias generating circuit are respectively connected with one pin of the MCU singlechip (5), one pin of the MCU singlechip (5) is connected between the resistor R4 and the resistor R5, and the automatic gain adjustment circuit is connected with the MCU singlechip (4) through the ADC circuit (4);

the automatic gain adjustment circuit comprises an amplifier OP2, a programmable and adjustable resistor U3, a programmable and adjustable resistor U4, a programmable and adjustable resistor U5 and a capacitor C6, wherein the inverting input terminal of the amplifier OP2, the programmable and adjustable resistor U3, the programmable and adjustable resistor U4, the programmable and adjustable resistor U5 and the output terminal of the amplifier OP2 are successively connected in series, both ends of the capacitor C6 are respectively connected with the inverting input terminal of the amplifier OP2 and the output terminal of the amplifier OP2, the inverting input terminal of the amplifier OP2 is connected with the programmable and adjustable resistor U1, the noninverting input terminal of the amplifier OP2 is connected with the resistor R4, and the output terminal of the amplifier OP2 is connected with the MCU singlechip (5) through the ADC circuit (4);

the automatic bias generating circuit comprises an MOS transistor Q2, a programmable and adjustable resistor U2, a programmable and adjustable resistor U6 and a capacitor C4, wherein the drain electrode D of the MOS transistor Q2, the capacitor C4, the programmable and adjustable resistor U6, the programmable and adjustable resistor U2 and the source electrode S of the MOS transistor Q2 are successively connected in series, the drain electrode D of the MOS transistor Q2 is connected with the inverting input terminal of the amplifier OP1, the gate electrode G of the MOS transistor Q2 is connected with one pin of the MCU singlechip (5), and there is a ground connection between the capacitor C4 and the programmable and adjustable resistor U6;

the programmable and adjustable resistor U1 is an X9C102 programmable resistor with a resistance value adjustable range of 0-1 KΩ the programmable and adjustable resistor U2, the programmable and adjustable resistor U3, the programmable and adjustable resistor U4, the programmable and adjustable resistor U5 and the programmable and adjustable resistor U6 are all X9C104 programmable resistors with a resistance value adjustable range of 0-100 KΩ;

the resistance value of the resistor R1 is 1 KΩ the resistance value of the resistor R2 is 10 KΩ the resistance value of the resistor R3 is 10 KΩ the resistance value of the resistor R4 is 47.5 KΩ and the resistance value of the resistor R5 is 27.4 KΩ; the capacitor C1 is a 10 nf capacitor, the capacitor C2 is a 10 nf capacitor, the capacitor C3 is a 10 nf capacitor, the capacitor C4 is a 10 nf capacitor, and the capacitor C5 is a 100 nf capacitor.

7. The wide-concentration multi-component hazardous gas detector according to claim 6, wherein a method for automatically identifying the electrochemical sensor (1) using the automatic identification and failure detection circuits of the electrochemical sensors (1) comprises the following steps:

Step ①: storing official information of an electrochemical sensor for fire protection in a storage, and establishing an electrochemical sensor database;

Step ②: detecting a no-load output value of a to-be-identified electrochemical sensor in an actual system and a characteristic value of an output curve during a power-on process through manual testing on the to-be-identified electrochemical sensor, and recording the tested no-load output value and the characteristic value into the storage;

Step ③: accessing the to-be-identified electrochemical sensor into the automatic identification and failure detection circuits of the electrochemical sensors (1), powering on the MCU singlechip (5), and the MCU singlechip (5) reads the no-load output value and the characteristic value of the to-be-identified electrochemical sensor from the storage;

Step ④: the MCU singlechip (5) respectively performs correct configuration on the automatic identification and failure detection circuits of the electrochemical sensors (1) according to the no-load output value and the characteristic value of the to-be-identified electrochemical sensor; and Step ⑤: the MCU singlechip (5) identifies the power-on of the to-be-identified electrochemical sensor through the automatic identification and failure detection circuits of the electrochemical sensors (1) and monitors voltage values of the to-be-identified electrochemical sensor at each period of time during the power-on process through the ADC circuit (4) meanwhile matching the monitored voltage values with the electrochemical sensors in the electrochemical sensor database in the storage, thereby automatically identifying the to-be-identified electrochemical sensor.

8. The wide-concentration multi-component hazardous gas detector according to claim 7, wherein a method for performing failure detection on an electrochemical sensor using the automatic identification and failure detection circuits of the electrochemical sensors (1) comprises the following steps:

Step I: accessing the to-be-identified electrochemical sensor into an automatic electrochemical sensor identification and failure detection system, and starting the automatic electrochemical sensor identification and failure detection system;

Step II: initializing the automatic electrochemical sensor identification and failure detection system;

Step III: changing parameters of the automatic electrochemical sensor identification and failure detection system after initialization is completed to allow a generation of ±1 mv perturbance in a bias of the to-be-detected electrochemical sensor; and Step IV: detecting whether the output voltage of the automatic electrochemical sensor identification and failure detection system changes with the perturbance in the bias of the to-be-detected electrochemical sensor, wherein if the output voltage has a perturbance amplitude larger than ±1 mv, the to-be-detected electrochemical sensor is detected as normal; if the output voltage has a perturbance amplitude smaller than ±1 mv, the to-be-detected electrochemical sensor is detected as failure.

* * * * *